US012594266B2

(12) United States Patent
Angulo Gonzalez et al.

(10) Patent No.: US 12,594,266 B2
(45) Date of Patent: Apr. 7, 2026

(54) **TRITERPENOID ANTIFUNGALS FOR THE TREATMENT OR PREVENTION OF *PNEUMOCYSTIS* SPP. PNEUMONIA**

(71) Applicant: Scynexis, Inc., Jersey City, NJ (US)

(72) Inventors: David A. Angulo Gonzalez, Palmetto Bay, FL (US); Stephen Andrew Barat, Mendham, NJ (US)

(73) Assignee: SCYNEXIS, INC., Jersey City, NJ (US)

( * ) Notice: Subject to any disclaimer, the term of this patent is extended or adjusted under 35 U.S.C. 154(b) by 803 days.

(21) Appl. No.: 17/432,926

(22) PCT Filed: Feb. 25, 2020

(86) PCT No.: PCT/US2020/019724

§ 371 (c)(1),
(2) Date: Aug. 21, 2021

(87) PCT Pub. No.: WO2020/176527

PCT Pub. Date: Sep. 3, 2020

(65) Prior Publication Data

US 2023/0149376 A1 May 18, 2023

Related U.S. Application Data

(60) Provisional application No. 62/811,456, filed on Feb. 27, 2019.

(51) Int. Cl.

| | |
|---|---|
| ***A61K 31/4439*** | (2006.01) |
| ***A61P 11/00*** | (2006.01) |
| ***A61P 31/10*** | (2006.01) |

(52) U.S. Cl.

CPC .......... *A61K 31/4439* (2013.01); *A61P 31/10* (2018.01)

(58) Field of Classification Search

CPC ....... A61K 31/4439; A61P 31/10; A61P 11/00

See application file for complete search history.

(56) References Cited

U.S. PATENT DOCUMENTS 5,166,135 A 11/1992 Schmatz

FOREIGN PATENT DOCUMENTS

WO WO-2019/028034 A1 2/2019

OTHER PUBLICATIONS

Cushion et al., P1226, SCY-078 demonstrates antifungal activity against pneumocystis in a prophylactic murine model of pneumocystis pneumonia, 28th European Congress of Clinical Microbiology and Infectious Diseases (ECCMID), XP055697357, Apr. 24, 2018.

"SCYNEXIS Data Presentations at ECCMID 2018 Show SCY-078 Potent and Synergistic Antifungal Activity Against Aspergillus and Pneumocystis," PRNewswire, XP055696797, Apr. 23, 2018.

International Search Report and Written Opinion for PCT/US2020/019724, dated Jun. 2, 2020.

*Primary Examiner* — Sun Jae Yoo

(74) *Attorney, Agent, or Firm* — Morgan, Lewis & Bockius LLP

(57) ABSTRACT

Eufumafungin derivative triterpenoid antifungal compounds are used to treat and/or prevent Pneumocystis pneumonia (PCP) due to their unexpected efficacy against *Pneumocystis* spp. including their ability to reduce the lung burden of cyst and trophic forms of this fungi. The enfumafungin derivative triterpenoids (or pharmaceutically acceptable salts or hydrates thereof) are inhibitors of (1,3)-β-D-glucan synthesis and are useful in the treatment and/or prevention of PCP since they demonstrate potent activity against *Pneumocystis* spp. in in vivo models, exhibit adequate tissue penetration into lungs, and are well tolerated.

16 Claims, 3 Drawing Sheets

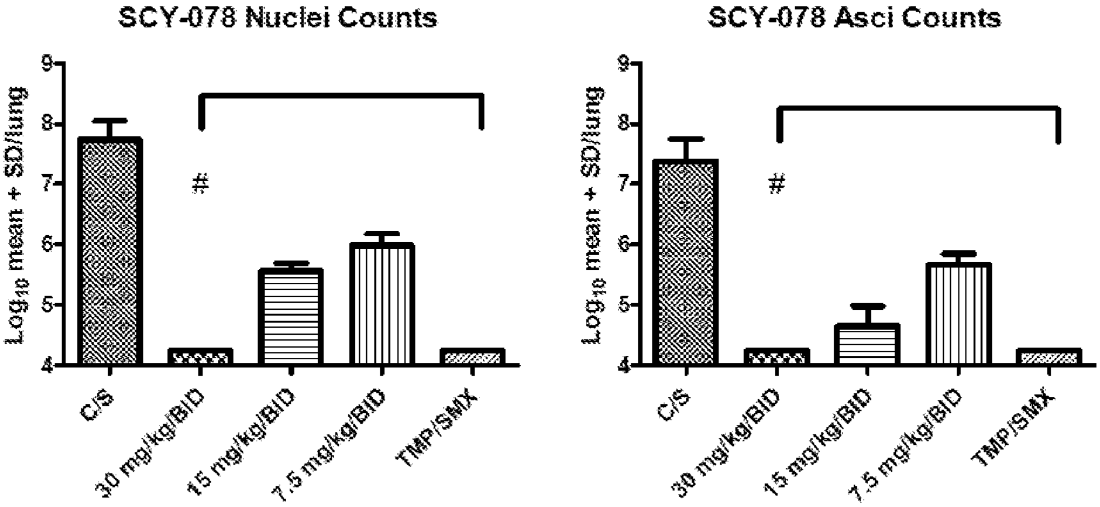

$Log_{10}$ mean nuclei and asci counts after 6 weeks of treatment. C/S, vehicle treated negative control. TMP/SMX, trimethoprim/sulfamethaxozole. Bracket denotes statistically significant difference between treatment groups and C/S group. # denotes no statistically significant difference between treatment group and TMP/SMX. Significance accepted with a P value ≤ 0.05.

FIG. 1

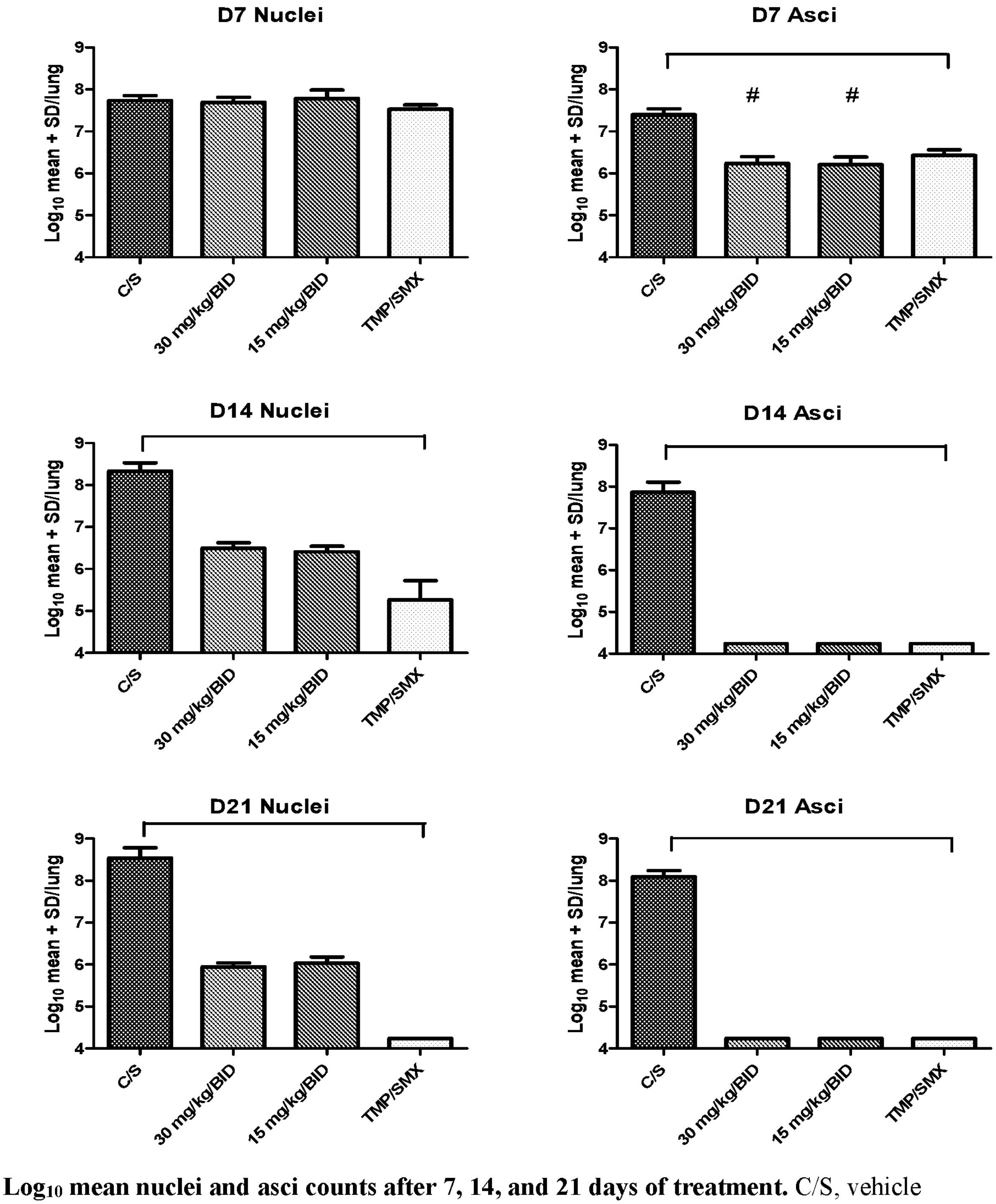

$Log_{10}$ mean nuclei and asci counts after 7, 14, and 21 days of treatment. C/S, vehicle treated negative control. TMP/SMX, trimethoprim/sulfamethoxazole. Bracket denotes statistically significant difference between treatment groups and C/S group. # denotes statistically significant difference between treatment group and TMP/SMX. Significance accepted with P value $\leq 0.05$.

FIG. 2

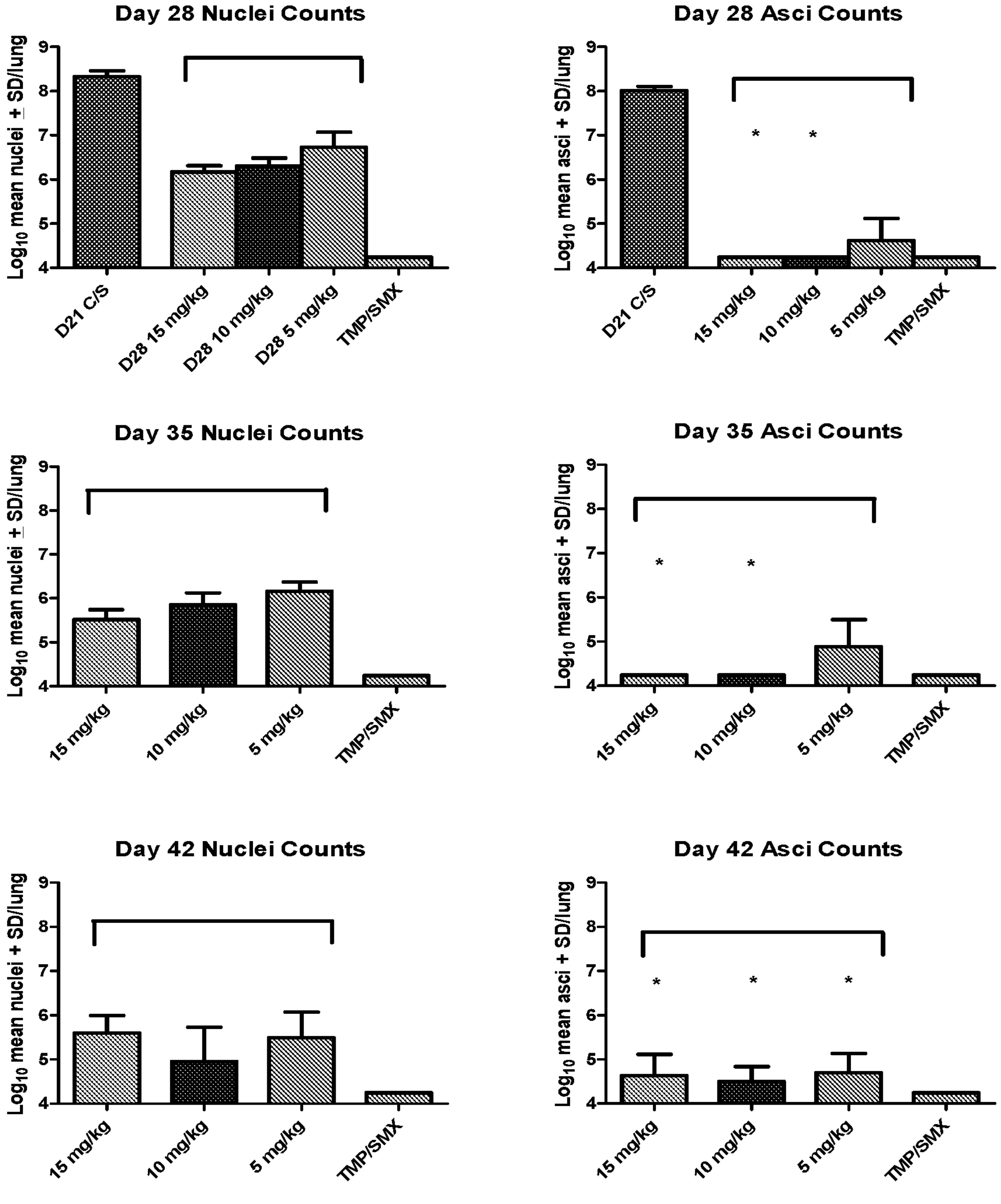

$Log_{10}$ mean nuclei and asci counts after 28, 35, and 42 days of treatment. C/S, vehicle treated negative control. TMP/SMX, trimethoprim/sulfamethoxazole. Bracket denotes statistically significant difference between treatment groups and C/S group. * denotes no statistically significant difference between treatment group and TMP/SMX. Significance accepted with a P value $\leq 0.05$.

FIG. 3

TRITERPENOID ANTIFUNGALS FOR THE TREATMENT OR PREVENTION OF *PNEUMOCYSTIS* SPP. PNEUMONIA

FIELD OF THE INVENTION

The present invention relates to the use of triterpenoid antifungals to treat and/or to prevent *Pneumocystis* spp. pneumonia. More particularly, the invention relates to the use of enfumafungin derivative triterpenoids (or pharmaceutically acceptable salts or hydrates thereof) that are inhibitors of (1,3)-β-D-glucan synthesis resulting in a deficiency in (1,3)-β-D-glucan (a fungal cell structure building block), in the treatment and/or the prevention of *Pneumocystis* spp. pneumonia. Currently available treatment options for *Pneumocystis* spp. pneumonia are limited and have significant associated toxicities. In contrast, the (1,3)-β-D-glucan synthase inhibitor ibrexafungerp (SCY-078) shows potent antifungal activity against *Pneumocystis* spp., exhibits adequate tissue penetration into lungs, and is well tolerated. In accordance with the present invention, the use of ibrexafungerp can provide advantages in the treatment and/or in the prevention of *Pneumocystis* spp. pneumonia.

BACKGROUND OF THE INVENTION

Fungal infections are a major healthcare problem and are most commonly manifested as invasive or systemic fungal disease (e.g., candidemia, invasive aspergillosis), mucocutaneous infections (e.g., oral, esophageal and vulvovaginal candidiasis) and localized fungal infections (e.g., pneumonia, pleural empyema and abscess localized in abdomen, brain, bone, etc.). The type and scope of the infection depends on the virulence factors of the fungal pathogen, the host's defenses, and the anatomic areas involved.

Severe systemic or invasive fungal infections are more common in immune-compromised patients such as patients receiving chemotherapy to treat malignancies, or receiving immunomodulatory agents to treat chronic inflammatory conditions, or suffering from immune deficiencies, either acquired (such as in the case of AIDS) or due to genetic disorders. Despite currently available antifungal therapies, systemic fungal infections are associated with a mortality rate of up to 50%, depending on the pathogen and the underlying condition of the patient.

Mucocutaneous fungal infections can occur in immunocompromised as well as in non-compromised individuals. The most common mucocutaneous fungal infections are vulvovaginal yeast infections, followed by oropharyngeal candidiasis and esophageal candidiasis, which are predominantly caused by species of *Candida.*

Localized fungal infections can occur in immuno-compromised as well as in non-compromised individuals and may originate via dissemination of the fungi from a local area where they normally colonize to an area that is normally sterile (e.g., abscess in abdominal cavity after gut perforation or surgery), from fungi entering the blood or lymphatic system that reaches a particular organ (e.g., lung, liver, spleen) or by acquisition from the environment (e.g., *Pneumocystis* spp. pneumonia) and that develops a deep seated infection.

*Pneumocystis* pneumonia (PCP) in humans is caused by *Pneumocystis jirovecii*, a ubiquitous fungus. *Pneumocystis jirovecii* is an opportunistic fungal organism that causes disease in individuals who are immuno-compromised, particularly those infected with human immunodeficiency virus (HIV). Although its incidence has decreased with the advent of anti-retroviral therapy (ART), PCP remains the most common opportunistic infection in patients with AIDS. Further, an increase in the non-HIV immuno-compromised population (including bone marrow transplant recipients and solid organ transplant recipients), noncompliance with current treatments, the emergence of drug-resistant *Pneumocystis jirovecii* strains, and a rise in HIV+ cases in developing countries all contribute toward making *Pneumocystis* a pathogen of continued interest and a public health concern. (Kelly M N, Shellito J E. Current understanding of *Pneumocystis* immunology. *Future Microbiol.* 2010 January: 5 (1): 43-65.)

*Pneumocystis jirovecii* was previously referred to as *Pneumocystis carinii*, but the taxonomy of the organism has been changed: *P. carinii* now properly refers only to the *Pneumocystis* species that infects rats, while *P. jirovecii* refers to the distinct species that infects humans. However, the abbreviation "PCP" is still used to designate *Pneumocystis* pneumonia. Initial infection with *P. jirovecii* usually occurs in early childhood: two-thirds of healthy children have antibodies to *P. jirovecii* by age 2 years to 4 years. Rodent studies and case clusters in immunosuppressed patients suggest that *Pneumocystis* spreads by the airborne route. Disease probably occurs by new acquisition of infection via the respiratory tract or reactivation of a latent infection. Before the widespread use of PCP prophylaxis and ART, PCP occurred in 70% to 80% of patients with AIDS: the course of treated PCP was associated with a 20% to 40% mortality rate in individuals with profound immunosuppression. Approximately 90% of PCP cases occurred in patients with CD4 T lymphocyte (CD4) cell counts of <200 cells/mm. The incidence of PCP has decreased but the mortality rate remains similar. Other factors associated with a higher risk of PCP include low CD4 cell percentage, previous episodes of PCP, oral thrush, recurrent bacterial pneumonia, unintentional weight loss, higher plasma HIV RNA levels, and immunosuppressive therapy. The incidence of PCP has declined with widespread use of PCP prophylaxis and ART, and most cases of PCP now occur in patients who are unaware of their HIV infection or are not receiving ongoing care for HIV, and in those with advanced immunosuppression due to other conditions such as malignancies.

The most common manifestations of PCP are subacute onset of progressive dyspnea, fever, non-productive cough, and chest discomfort that worsens within days to weeks and may result in fatal respiratory failure, although fast-progressing fulminant pneumonia can also occur. Because blood tests and chest radiographs are not pathognomonic for PCP (and because the organism cannot be cultivated routinely), histopathologic or cytopathologic or molecular demonstration of organisms in tissue, bronchoalveolar lavage (BAL) fluid, or induced sputum samples is required for a definitive diagnosis of PCP.

Treatment with an antimicrobial agent with activity against *Pneumocystis* should be initiated as soon as the diagnosis is made. Because of the potentially fatal consequences of the disease, immune-compromised patients at high risk of developing this infection often receive preventive administration of an antimicrobial agent (prophylaxis) while they are at risk, which could be several months. Trimethoprim-sulfamethoxazole (TMP-SMX) (written also as trimethoprim/sulfamethoxazole: TMP/SMX) is the currently recommended antimicrobial agent for prevention and treatment of PCP. However, there is a high incidence of intolerance to this drug, and serious and sometimes life-threatening adverse reactions are reported after TMP-SMX use. These undesirable reactions often lead to interruption or permanent discontinuation of TMP-SMX. In patients with HIV, rates of adverse reaction to TMP-SMX are high (20% to 85% of patients). Common adverse effects are rash (30% to 55% of patients) (including Stevens-Johnson syndrome), fever (30% to 40% of patients), leukopenia (30% to 40% of patients), thrombocytopenia (15% of patients), azotemia (1% to 5% of patients), hepatitis (20% of patients), and hyperkalemia. (Guidelines for the Prevention and Treatment of Opportunistic Infections in Adults and Adolescents with HIV, *Pneumocystis* Pneumonia, Last Updated: Mar. 28, 2019; Last Reviewed: Jun. 26, 2019. https://aidsinfo.nih.gov/guidelines/html/4/adult-and-adolescent-opportunistic-infection/321/*pneumocystis*-pneumonia.) While there are alternative therapies when TMP-SMX is not tolerated, such therapies have not shown the same efficacy in all settings and are also associated with significant toxicity. The most common adverse effects of alternative therapies include methemoglobinemia and hemolysis with dapsone or primaquine (especially in those with G6PD deficiency); rash and fever with dapsone: azotemia, pancreatitis, hypoglycemia or hyperglycemia, leukopenia, electrolyte abnormalities, and cardiac dysrhythmia with pentamidine: anemia, rash, fever, and diarrhea with primaquine and clindamycin; and headache, nausea, diarrhea, rash, and transaminase elevations with atovaquone.

In addition, nonadherence to therapy and/or long-term prophylaxis use in *Pneumocystis*-colonized individuals have led to the selection of mutations giving rise to drug-resistant strains. These include mutations in the targets for trimethoprim and pyrimethamine, atovaquone and sulfa drugs, leading to treatment failure and increased mortality. (Kelly M N, Shellito J E. Current understanding of *Pneumocystis* immunology. *Future Microbiol.* 2010 January: 5 (1): 43-65.) With drug resistance threatening the most effective existing treatments, novel therapies are in great demand.

Previously classified as protozoan, *Pneumocystis* spp. are yeast-like fungi that reside extracellularly in the lung alveoli and can infect mammals, with *P. jirovecii* infecting humans, *P. carinii* rats, and *P. murina* mice. In contrast with other fungi, *Pneumocystis* cannot be cultured in vitro in typical fungal growth media, and most of what is known of its life cycle comes from observations in animal models of infection. The inability to culture the organism in vitro has been a major obstacle to studying therapies for this opportunistic infection, and most research relies on in vivo observations. Within the mammalian host, *Pneumocystis* has a tropism for the alveoli. Microscopic observations and molecular genetic studies suggest a life cycle that includes an asexual mode of replication via binary fission of the amoeba-like trophozoite (trophic) form and a sexual mode resulting in formation of an ascus (cyst) containing eight ascospores.

PCP currently has limited treatment options. Standard antifungal drugs targeting ergosterol and ergosterol biosynthesis, such as amphotericin B and the azoles, are ineffective. The echinocandins (caspofungin, anidulafungin, and micafungin) inhibit synthesis of (1,3)-β-D-glucan, an essential component of the cell wall of many fungi, including the cyst form of *Pneumocystis* spp. However, reports on the efficacy of echinocandins on PCP in patients reveal uncertainties and limitations with this class of agents. A murine model (Cushion M T, Linke M J, Ashbaugh A, Sesterhenn T, Collins M S, Lynch K, Brubaker R, Walzer P D. Echinocandin treatment of *pneumocystis* pneumonia in rodent models depletes cysts leaving trophic burdens that cannot transmit the infection. *PLoS One.* 2010 Jan. 29; 5 (1): e8524) assessing the activity of the echinocandins on murine PCP showed that parenteral (intraperitoneal) administration of echinocandin for 3 weeks significantly reduced cyst burdens versus in untreated mice. No dose response was observed for any echinocandin. In contrast to the noticeable reductions of cysts, large numbers of trophic forms remained in the lungs of treated mice, often reaching levels that were not significantly different from untreated controls. There were differences in the response to each echinocandin, with caspofungin being the most effective and micafungin the least effective with no significant reduction in trophic burden at any dose of micafungin versus in untreated control mice. These observations suggest that the echinocandins may have an effect on the cyst form of *Pneumocystis* spp. but their effect on the trophic form of the fungi is less clear and is likely compound-specific.

The echinocandins are not currently indicated for the treatment or prevention of PCP, although isolated reports have documented its use in the clinical setting alone or in combination with TMP-SMX, in most instances as salvage therapy, with variable results, underscoring the importance of developing new antifungal agents to treat this fungal infection. (Zhang G et al. Efficacy of caspofungin combined with trimethoprim/sulfamethoxazole as first-line therapy to treat non-HIV patients with severe *pneumocystis* pneumonia. Exp Ther Med. 2018 February: 15 (2): 1594-1601. Huang Y S et al. Echinocandins as alternative treatment for HIV-infected patients with *Pneumocystis* pneumonia. *AIDS.* 2019 Jul. 1; 33 (8): 1345-1351.) Other limitations of echinocandins as potential alternatives for the treatment or prevention of PCP are that they are only available in intravenous form, and the treatment or prevention of PCP often requires several weeks or months of therapy. Long-term IV administration is not optimal and often is not feasible. Moreover, in line with the low volume of distribution reported for the three echinocandins, ranging from 0.15 to 0.8 liters/kg, the tissue concentrations achieved in lung are typically lower than in plasma (Felton T, Troke P F, Hope W W. Tissue penetration of antifungal agents. *Clin Microbiol Rev.* 2014 January: 27 (1): 68-88), which may result in sub-efficacious concentrations at the site of infection (i.e., lung).

Enfumafungin is a hemiacetal triterpene glycoside that is produced in fermentations of a *Hormonema* spp. associated with living leaves of *Juniperus communis* (U.S. Pat. No. 5,756,472; Pelaez et al., *Systematic and Applied Microbiology,* 23:333-343 (2000): Schwartz et al., JACS, 122:4882-4886 (2000): Schwartz, R. E., *Expert Opinion on Therapeutic Patents,* 11 (11): 1761-1772 (2001)). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy,* 44:368-377 (2000): Pelaez et al., (2000)). 1,3-β-D-glucan synthase remains an attractive target for antifungal drug action because it is present in many pathogenic fungi and therefore affords a broad antifungal spectrum. In addition, because there is no mammalian counterpart to (1,3)-β-D-glucan synthase, the enfumafungin derivatives described herein have little or no mechanism-based toxicity. The triterpenoid compound derivatives of enfumafungin used according to this invention have demonstrated activity against fungal isolates of *Candida* spp., including those isolates that are resistant to azoles or other glucan synthase inhibitors (e.g., lipopeptides agents such echinocandins), indicating that the biological and molecular target of the enfumafungin derivatives is different from that of other glucan synthase inhibitors.

Various enfumafungin derivatives have been disclosed, e.g., in International Patent Publication Nos. WO 2007/126900 and WO 2007/127012.

Certain representatives of these enfumafungin derivatives can be administered orally, have shown antifungal activity against *Candida* and *Aspergillus* species, and have shown adequate distribution into tissues, including lung tissues. (Wring S, Borroto-Esoda K, Solon E, Angulo D. 2019. SCY-078, a novel fungicidal agent, demonstrates distribution to tissues associated with fungal infections during mass balance studies with intravenous and oral [1+C]SCY-078 in albino and pigmented rats. *Antimicrob Agents Chemother* 63: e02119-18. https://doi.org/10.1128/AAC.02119-18.)

The ability of an antifungal drug to be distributed into lung tissues is relevant to the treatment or prevention of PCP. The ability of SCY-078, a representative compound of enfumafungin derivatives described herein, to be distributed into lung tissues was evaluated in an animal model. Id. Male albino Wistar Han (WH; Charles River, Raleigh, NC) (n=38) or male (n=18) and female (n=3) pigmented Long-Evans (LE; Hilltop Lab Animals, Inc., Scottdale, PA) rats received [14C]SCY-078 by oral administration (15 mg/kg. ~150) μCi/kg, in aqueous 0.5% methylcellulose) or i.v. administration (5 mg/kg, ~108 μCi/kg. 7.5:1 molar ratio of Captisol: SCY-078 in saline) as a 1-h infusion (10 ml/kg/h). WH rats were used for mass balance and pharmacokinetic (PK) determinations after i.v. and oral doses, and both WH and LE rats were used for Quantitative whole-body autoradiography (QWBA) determinations. Dose levels were selected to reflect the clinically relevant 11.2-μg·h/ml target exposure for *Candida* spp. infections. The concentration, homogeneity, radio purity, and stability of dosing formulations were confirmed to be acceptable before dosing. For QWBA whole-body sections (~40 μm thick via Leica CM3600 cryomicrotome; Nussloch, Germany), where all major tissues, organs, and biological fluids were represented, sections were exposed for phosphor imaging (Fuji Biomedical, Stamford, CT) together with calibration standards. Animals were deeply anesthetized with isoflurane anesthesia and, after blood samples were obtained, were euthanized by freezing in a hexane/solid carbon dioxide bath for at least 15 min. The imaging plate was scanned with the GE Healthcare Typhoon FLA 9500 image acquisition system (GE/Molecular Dynamics, Sunnyvale, CA).

Quantification was performed by image densitometry with MCID image analysis software (v. 7.0; Interfocus Imaging Ltd., Linton, Cambridge, UK), and a standard curve was constructed from the integrated response (molecular dynamics counts [MDC]/$mm^2$) and the nominal concentrations of the $^{14}C$-calibration standards. The concentrations of radioactivity were expressed as [1+C]SCY-078 μg equiv/g tissue. The lower limit of quantitation was 0.024 and 0.049 μg equiv/g of tissue for i.v. and oral doses of SCY-078, respectively.

Tissue to blood AUC ratios of total radioactivity after 15 mg/kg oral dose of [$^{14}C$]-SCY-078 to male pigmented Long-Evans rats are illustrated in the table below:

| Sample | $AUC_{all}$ (μg equiv*h/g) | Tissue:Blood AUC Ratio |
|---|---|---|
| Adrenal gland | 321.126 | 48.431 |
| Blood (cardiac) | 6.631 | 1.000 |
| Bone | 9.022 | 1.361 |
| Bone marrow (femur) | 238.388 | 35.953 |
| Brain (cerebrum) | 0.727 | 0.110 |
| Cecum | 83.542 | 12.600 |
| Epididymis | 75.355 | 11.365 |
| Esophagus | 41.430 | 6.248 |
| Exorbital gland | 523.676 | 78.980 |
| Eye (lens) | 0.084 | 0.013 |
| Eye (uvea) | 777.035 | 117.191 |
| Heart (myocardium) | 66.558 | 10.038 |
| Kidney (cortex) | 165.880 | 25.018 |
| Kidney (medulla) | 136.610 | 20.603 |
| Large intestine | 57.682 | 8.727 |
| Liver | 374.517 | 56.484 |
| Lung | 175.593 | 26.483 |
| Lymph node | 251.036 | 37.861 |
| Oral mucosa | 36.782 | 5.547 |
| Pancreas | 110.455 | 16.659 |
| Pituitary | 640-809 | 96.645 |
| Prostate gland | 61.301 | 9.245 |
| Salivary gland | 149.193 | 22.501 |
| Seminal vesicle | 26.827 | 4.046 |
| Skeletal muscle | 28.304 | 4.269 |
| Skin (non-pigmented) | 74.884 | 11.294 |
| Skin (pigmented) | 110.249 | 16.627 |
| Small intestine | 141.607 | 21.357 |
| Spleen | 507.638 | 75.561 |
| Stomach (gastric mucosa) | 181.074 | 27.309 |
| Testis | 64.972 | 9.799 |
| Thymus | 195.608 | 29.501 |
| Thyroid | 291.187 | 43.916 |
| Urinary bladder | 45.955 | 6.931 |

The exposure observed in lung exceeded by more than 20-fold the exposure measured in plasma in this study.

The safety and tolerability of SCY-078 has been evaluated in more than 900 subjects in ~20 clinical trials, at different doses and treatment durations, including administration for up to 1 year. The most common adverse events have been mild to moderate, transient gastrointestinal disorders such as nausea, diarrhea and abdominal pain. Serious adverse events possibly related to SCY-078 have been very rare and interruption or discontinuation of therapy due to adverse reactions has been uncommon. Additionally, the safety profile of oral SCY-078 has been evaluated in standard long-term non-clinical toxicology studies including administration for 9 months in dogs and 6 months in rats, at doses and exposures higher than those anticipated in humans, in line with ICH guidelines. The results from these non-clinical studies support the long-term administration of oral SCY-078 in humans. SCY-078 is currently under evaluation in ongoing clinical trials for the treatment of fungal infections such as candidiasis and aspergillosis. SCY-078 has not been evaluated in clinical trials for the treatment or prevention of PCP.

Given the limited number of antimicrobials available to treat or prevent PCP, the significant and sometime life-threatening toxicities exhibited by currently approved compounds, and the increasing incidence of *P. jirovecii* resistance to currently available antimicrobial options, there is a need in the art for antifungal therapy that is effective for the treatment and prevention of PCP in humans and that can be administered safely and conveniently for the frequently long-term dosing duration required to prevent and treat this infection.

SUMMARY OF THE INVENTION

The enfumafungin derived triterpenoid compound SCY-078 or ibrexafungerp—a representative compound of enfumafungin derivatives described herein—shows a high level of efficacy in the treatment and/or prevention of PCP, in murine models. SCY-078 shows potent antifungal activity against *Pneumocystis* spp., exhibits adequate tissue penetration into lungs, and is well tolerated. In accordance with the present invention, SCY-078 or ibrexafungerp can be used to treat and/or prevent *Pneumocystis* spp. pneumonia in humans.

SCY-078 unexpectedly demonstrated pharmacologic activity equivalent to the positive control, Bactrim® (trimethoprim/sulfamethoxazole), which is the current gold standard for treatment of PCP. More surprisingly, the compound showed burden reduction of both cyst (asci) and trophic forms (nuclei). The life-cycles of *Pneumocystis* spp. exist in two forms: cysts and trophs. The cystic form has a (1,3)-β-D-glucan-containing cell wall, whereas this feature is absent in the trophic form. Although the role of each form of the fungi (cyst and trophic) in human disease is not fully elucidated, it is considered that inhibition of both forms is optimal to control the PCP infection and prevent dissemination. In accordance with the present invention, SCY-078 as an inhibitor of (1,3)-β-D-glucan synthase resulted in pharmacologic effect on the cystic form, e.g., a reduction in cyst burden. Surprisingly, treatment with SCY-078 also resulted in a significant reduction in nuclei (nuclei are indicative of troph burdens). Furthermore, reductions in cysts and trophs occurred in both the prophylaxis and treatment models of PCP.

The compound unexpectedly demonstrated enhanced penetration into lung when compared to other (1,3)-β-D-glucan synthase inhibitors. SCY-078 can be administered orally, which provides an advantage in the prevention and treatment of PCP, given that long-term antifungal administration is typically needed in the case of PCP.

The present invention relates to using enfumafungin derivatives for the treatment and/or prevention of PCP. Enfumafungin derivatives, and pharmaceutically acceptable salts or hydrates thereof, are useful in the inhibition of (1,3)-β-D-glucan synthase, and are particularly useful in treatment and/or prevention of PCP, which is an infection where potent antifungal activity is needed in the art.

The present invention addresses needs in the art such as those described above because the enfumafungin derivatives described herein (a) unexpectedly achieved high efficacy in the treatment and the prevention of PCP, (b) showed activity against both *P. jirovecii* forms (cyst and trophic), (c) surprisingly achieved concentrations in lung that are several-fold higher than in plasma, (d) can be administered orally allowing for optimal therapy in these infections which often require several months of therapy, and (e) were well tolerated, allowing for safe administration over long periods of time.

Applications of this invention include but are not limited to the ability to more easily achieve a successful outcome in the treatment and/or prevention of PCP because of the reasons outlined above.

The present invention provides the use of a compound of Formula (I), or a pharmaceutically acceptable salt or hydrate thereof:

(I)

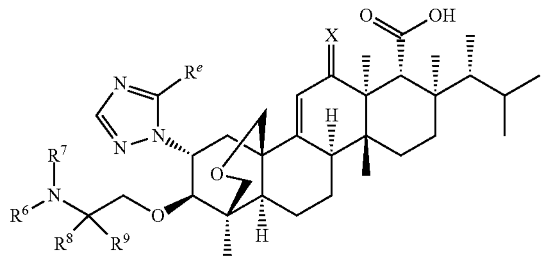

wherein:

X is O or H, H:

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen:

$R^f$, $R^g$, $R^6$ and $R^7$ are each independently hydrogen or $C_1$-$C_3$ alkyl:

$R^8$ is $C_1$-$C_4$ alkyl, $C_3$-$C_4$ cycloalkyl or $C_4$-$C_5$ cycloalkyl-alkyl:

$R^9$ is methyl or ethyl; and $R^8$ and $R^9$ are optionally taken together to form a 6-membered saturated ring containing 1 oxygen atom, in a subject for the treatment and/or prevention of PCP.

The invention also provides methods of treating and/or preventing PCP in a subject by administering the compound of Formula (I) or a pharmaceutically acceptable salt or hydrate thereof. Further, the invention provides the use of a compound of Formula (I) or a pharmaceutically acceptable salt or hydrate thereof in the preparation of a medicament for the treatment and/or prevention of PCP in a subject.

With the present invention, enfumafungin derived triterpenoid antifungal agents can reduce both troph burden (as evidenced by reductions in nuclei) and cyst burden (as evidenced by reductions in asci) in a *Pneumocystis* spp. model of infection.

BRIEF DESCRIPTION OF THE DRAWINGS

FIG. 1 is a graph of $\log_{10}$ mean nuclei and asci counts after a 6-week study showing that prophylaxis administration of SCY-078 resulted in a statistically significant reduction of both nuclei and asci counts when compared to untreated controls.

FIG. 2 is a graph of $\log_{10}$ mean nuclei and asci counts after 7, 14, and 21 days of treatment with SCY-078 compared with untreated controls and TMP/SMX.

FIG. 3 is a graph of $\log_{10}$ mean nuclei and asci counts after 28, 35, and 42 days of treatment with SCY-078 compared with untreated controls and TMP/SMX.

DETAILED DESCRIPTION OF THE INVENTION

The present invention relates to the use of enfumafungin derivative triterpenoid antifungal compounds to treat and/or prevent *Pneumocystis* spp. pneumonia. More particularly, the invention relates to the use of enfumafungin derivative triterpenoids (or pharmaceutically acceptable salts or hydrates thereof) that are inhibitors of (1,3)-β-D-glucan synthesis, in the treatment and/or prevention of PCP for which adequate tolerability to long-term antifungal therapy (more than 4 weeks) is needed, burden reduction of cyst and trophic forms of *P. jirovecii* is desirable, and sufficient antifungal penetration into the affected tissues is needed, for treatment and/or prevention of the infection. The present invention provides a needed, advantageous alternative to trimethoprim/sulfamethoxazole (TMP/SMX), which is currently considered the treatment of choice for PCP but which is limited by significant toxicities associated with its use (with the few other currently available options all having meaningful safety concerns as well). The enfumafungin derivative triterpenoids described herein show potent antifungal activity against *Pneumocystis* spp., exhibit adequate tissue penetration into lungs, and are well tolerated, providing advantages in the treatment and/or prevention of *Pneumocystis* spp. pneumonia.

The present invention provides the use of a compound of Formula (I), or a pharmaceutically acceptable salt or hydrate thereof:

(I)

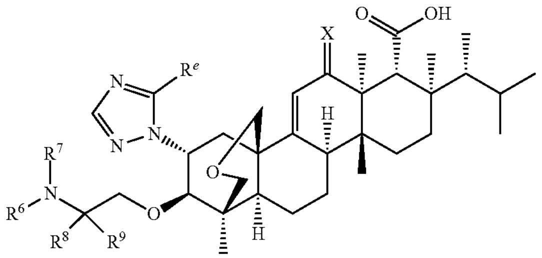

wherein:

X is O or H, H;

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkyl-alkyl;

$R^9$ is methyl or ethyl; and $R^8$ and $R^9$ are optionally taken together to form a 6-membered saturated ring containing 1 oxygen atom, in a subject for the treatment and/or prevention of PCP.

The invention also provides methods of treating and/or preventing PCP in a subject by administering the compound of Formula (I) or a pharmaceutically acceptable salt or hydrate thereof. Further, the invention provides the use of a compound of Formula (I) or a pharmaceutically acceptable salt or hydrate thereof in the preparation of a medicament for the treatment and/or prevention of PCP in a subject.

The present invention also provides the use of a compound of Formula (Ia), or a pharmaceutically acceptable salt or hydrate thereof:

(Ia)

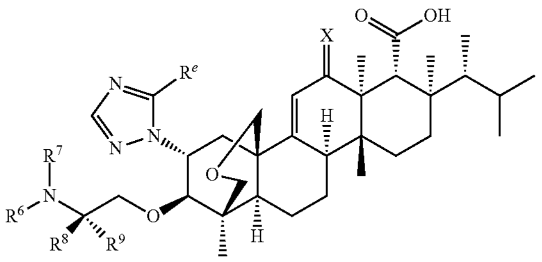

wherein the substituents are as provided for in Formula (I), in a subject for the treatment and/or prevention of PCP.

The invention also provides methods of treating and/or preventing PCP in a subject by administering the compound of Formula (Ia) or a pharmaceutically acceptable salt or hydrate thereof. Further, the invention provides the use of a compound of Formula (Ia) or a pharmaceutically acceptable salt or hydrate thereof in the preparation of a medicament for the treatment and/or prevention of PCP in a subject.

In embodiment 1: X is H, H, and the other substituents are as provided in Formula (I).

In embodiment 2: $R^e$ is either pyridyl or pyrimidinyl optionally mono-substituted on a ring carbon with fluoro or chloro or on a ring nitrogen with oxygen, and the other substituents are as provided in embodiment 1 or in Formula (I).

In embodiment 3: $R^e$ is 4-pyridyl and the other substituents are as provided in embodiment 1 or in Formula (I).

In embodiment 4: $R^e$ is $C(O)NH_2$ or $C(O)NH(C_1$-$C_3$ alkyl) and the other substituents are as provided in embodiment 1 or in Formula (I).

In embodiment 5: $R^8$ is $C_1$-$C_4$ alkyl and $R^9$ is methyl; and the other substituents are as provided in embodiment 1, 2, 3, or 4, or in Formula (I).

In embodiment 6: $R^8$ is t-butyl, $R^9$ is methyl; and the other substituents are as provided in embodiment 1, 2, 3, or 4, or in Formula (I).

In embodiment 7: $R^6$ and $R^7$ are each independently hydrogen or methyl and the other substituents are as provided in embodiment 1, 2, 3, 4, 5, or 6, or in Formula (I).

In embodiment 1': X is H, H, and the other substituents are as provided for in Formula (Ia).

In embodiment 2': $R^e$ is either pyridyl or pyrimidinyl optionally mono-substituted on a ring carbon with fluoro or chloro or on a ring nitrogen with oxygen, and the other substituents are as provided in embodiment 1' or in Formula (Ia).

In embodiment 3': $R^e$ is 4-pyridyl and the other substituents are as provided in embodiment 1' or in Formula (Ia).

In embodiment 4': $R^e$ is $C(O)NH_2$ or $C(O)NH(C_1$-$C_3$ alkyl) and the other substituents are as provided in embodiment 1' or in Formula (Ia).

In embodiment 5': $R^8$ is $C_1$-$C_4$ alkyl and $R^9$ is methyl; and the other substituents are as provided in embodiment 1', 2', 3', or 4', or in Formula (Ia).

In embodiment 6': $R^8$ is t-butyl, R' is methyl; and the other substituents are as provided in embodiment 1', 2', 3', or 4', or in Formula (Ia).

In embodiment 7': $R^6$ and $R^7$ are each independently hydrogen or methyl and the other substituents are as provided in embodiment 1', 2', 3', 4', 5', or 6', or in Formula (Ia).

In preferred embodiments, the present invention provides the use of a compound of Formula (II):

(II)

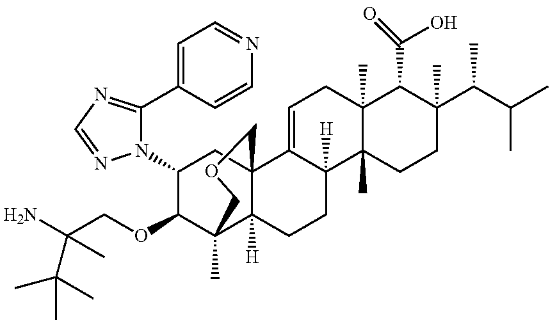

which is (1S,4aR,6aS,7R,8R,10aR,10bR,12aR, 14R, 15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a, 7,8,9,10,10a, 10b, 11,12,12a-dodecahydro-1,6a,8,10a-tetramethyl-4H-1,4a-propano-2H-phenanthro [1,2-c]pyran-7-carboxylic acid, or a pharmaceutically acceptable salt or hydrate thereof, in a subject for the treatment and/or prevention of PCP.

The invention also provides methods of treating and/or preventing PCP in a subject by administering the compound of Formula (II) or a pharmaceutically acceptable salt or hydrate thereof. Further, the invention provides the use of a compound of Formula (II) or a pharmaceutically acceptable salt or hydrate thereof in the preparation of a medicament for the treatment and/or prevention of PCP in a subject.

In other preferred embodiments, the present invention provides the use of a compound of Formula (IIa) (herein referred to as SCY-078 or ibrexafungerp):

(IIa)

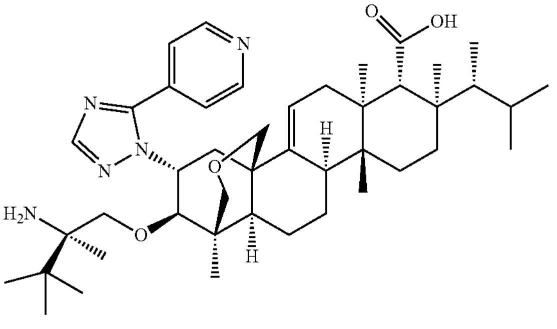

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a, 7,8,9,10,10a, 10b, 11,12,12a-dodecahydro-1,6a, 8,10a-tetramethyl-4H-1,4a-propano-2H-phenanthro [1,2-c] pyran-7-carboxylic acid, or a pharmaceutically acceptable salt or hydrate thereof, in a subject for the treatment and/or prevention of PCP.

The invention also provides methods of treating and/or preventing PCP in a subject by administering the compound of Formula (IIa) or a pharmaceutically acceptable salt or hydrate thereof. Further, the invention provides the use of a compound of Formula (IIa) or a pharmaceutically acceptable salt or hydrate thereof in the preparation of a medicament for the treatment and/or prevention of PCP in a subject.

In preferred embodiments, the phosphate salt of a compound of Formula (I), (Ia), (II), or (IIa) is used or administered as described herein.

In preferred embodiments, the citrate salt of a compound of Formula (I), (Ia), (II), or (IIa) is used or administered as described herein.

In preferred embodiments, the compounds of Formula (I), (la), (II), and (IIa), or pharmaceutically salts or hydrate forms thereof, are administered orally.

In preferred embodiments, the compounds of Formula (I), (la), (II), and (IIa), or pharmaceutically salts or hydrate forms thereof, are administered intravenously.

The present invention also provides the use of a pharmaceutical composition comprising a compound of Formula (I), (Ia), (II), or (IIa), or a pharmaceutically acceptable salt or hydrate thereof, and a pharmaceutically acceptable carrier, adjuvant, or vehicle, in a subject for the treatment and/or prevention of PCP.

The present invention also provides methods of treating and/or preventing PCP in a subject by administering a pharmaceutical composition comprising the compound of Formula (I), (Ia), (II), or (IIa), or a pharmaceutically acceptable salt or hydrate thereof, and a pharmaceutically acceptable carrier, adjuvant, or vehicle.

The present invention provides methods for treating and/or preventing PCP, comprising administering an effective amount of a compound of Formula (I), (Ia), (II), or (IIa) (or a pharmaceutically acceptable salt or hydrate thereof).

In the description of compounds in the embodiments set forth above, indicated substitutions are included only to the extent that the substituents provide stable compounds consistent with the definition.

The compounds of Formula (I), (Ia), (II), and (IIa), and pharmaceutically acceptable salts and hydrate forms thereof, have antimicrobial (e.g., antifungal) activities against yeasts and other fungi, including one or more of *Acremonium, Absidia* (e.g., *Absidia corymbifera*), *Alternaria, Aspergillus* (e.g., *Aspergillus clavatus, Aspergillus flavus, Aspergillus fumigatus, Aspergillus nidulans, Aspergillus niger, Aspergillus terreus*, and *Aspergillus versicolor*), *Bipolaris, Blastomyces* (e.g., *Blastomyces dermatitidis*), *Blastoschizomyces* (e.g., *Blastoschizomyces capitatus*), *Candida* (e.g., *Candida albicans, Candida auris, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cladosporium* (e.g., *Cladosporium carrionii* and *Cladosporium* trichloides), *Coccidioides* (e.g., *Coccidioides immitis*), *Cryptococcus* (e.g., *Cryptococcus neoformans*), *Curvularia, Cunninghamella* (e.g., *Cunninghamella elegans*), *Dermatophyte, Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candidum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor, Paracoccidioides* (e.g., *Paracoccidioides brasiliensis*), *Penicillium* (e.g., *Penicillium marneffei*), *Phialophora, Pityrosporum ovale, Pneumocystis* (e.g., *Pneumocystis jirovecii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedospo-*

*rium* (e.g., *Scedosporium apiosperum*), *Scopulariopsis, Sporothrix* (e.g., *Sporothrix schenckii*), *Trichoderma, Trichophyton* (e.g., *Trichophyton mentagrophytes* and *Trichophyton rubrum*), and *Trichosporon* (e.g., *Trichosporon asahii, Trichosporon beigelii*, and *Trichosporon cutaneum*).

The compounds of Formula (I), (Ia), (II), and (IIa), and pharmaceutically acceptable salts and hydrate forms thereof, can be made according to the synthesis methods disclosed in U.S. Pat. No. 8,188,085, the contents of which are hereby incorporated by reference in their entirety.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec-and t-butyl, n-and isopropyl, ethyl and methyl. As another example, "$C_{14}$ alkyl" refers to n-, iso-, sec-and t-butyl, n-and isopropyl, ethyl and methyl.

The term "cycloalkyl" refers to any cyclic ring of an alkane having a number of carbon atoms in the specified range. Thus, for example, "$C_{3-4}$ cycloalkyl" (or "$C_3$-$C_4$ cycloalkyl") refers to cyclopropyl and cyclobutyl.

The term "cycloalkyl-alkyl" (or equivalently "alkyl-cycloalkyl") as used herein refers to a system that includes an alkyl portion as described above and also includes a cycloalkyl portion as described above. Attachment to a "cycloalkyl-alkyl" (or "alkyl-cycloalkyl") may be through either the cycloalkyl or the alkyl portion. The specified number of carbon atoms in "cycloalkyl-alkyl" systems refers to the total number of carbon atoms in both the alkyl and the cycloalkyl parts. Examples of $C_4$-$C_5$ cycloalkyl-alkyl include but are not limited to methylcyclopropyl, dimethylcyclopropyl, methylcyclobutyl, ethylcyclopropyl, cyclopropylmethyl, cyclopropylethyl and cyclobutylmethyl.

The term "halogen" (or "halo") refers to fluorine, chlorine, bromine and iodine (alternatively referred to as fluoro, chloro, bromo, and iodo).

The term "or" as used herein denotes alternatives that may, where appropriate, be combined.

Unless expressly stated to the contrary, all ranges cited herein are inclusive. For example, a heterocyclic ring described as containing from "1 to 4 heteroatoms" means the ring can contain 1, 2, 3, or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5-or 6-membered heteroaromatic rings include, but are not limited to, pyridyl, pyrazinyl, pyrimidinyl, pyridazinyl and triazolyl.

A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject). Reference to a compound also includes stable complexes of the compound such as a stable hydrate.

As a result of the selection of substituents and substituent patterns, certain of the compounds of Formula (I), (Ia), (II), and (IIa) can have asymmetric centers and can occur as mixtures of stereoisomers, or as individual diastereomers, or enantiomers. Unless otherwise indicated, all isomeric forms of these compounds (and pharmaceutically acceptable salts and hydrate forms thereof), whether isolated or in mixtures, are within the scope of the present invention. Also included within the scope of the present invention are tautomeric forms of the compounds as depicted (and pharmaceutically acceptable salts and hydrate forms thereof).

When any variable occurs more than one time in any constituent or in Formula (I), (Ia), (II), or (IIa), its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

A bond terminated by a wavy line is used herein to signify the point of attachment of a substituent group or partial structure. This usage is illustrated by the following example:

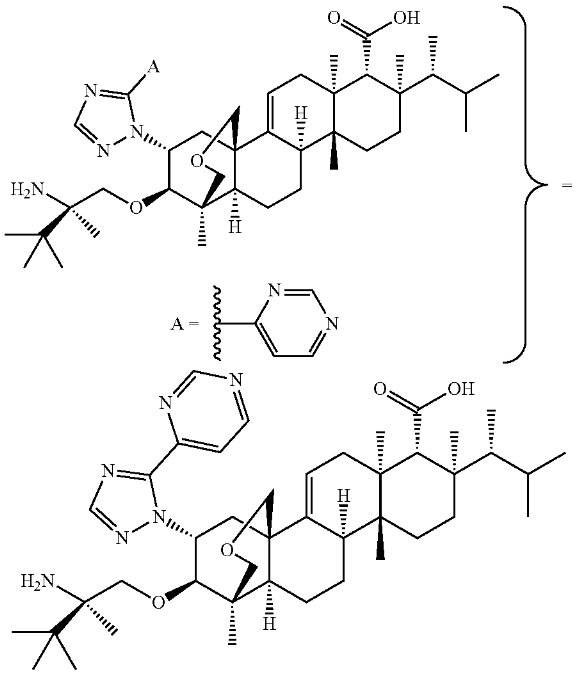

The compounds of Formula (I), (Ia), (II), and (IIa), and pharmaceutically acceptable salts and hydrate forms thereof, are also useful in the preparation and execution of screening assays for antifungal compounds. For example, the compounds are useful for isolating mutants, which are excellent screening tools for identifying further antifungal compounds.

The compounds of Formula (I), (Ia), (II), and (IIa) may be administered in the form of "pharmaceutically acceptable salts" or hydrates as appropriate. Other salts may, however, be useful in the preparation of the compounds or of their pharmaceutically acceptable salts. For example, when the compounds contain a basic amine group, they may be conveniently isolated as trifluoroacetic acid salts (e.g., following HPLC purification). Conversion of the trifluoroacetic acid salts to other salts, including pharmaceutically acceptable salts, may be accomplished by a number of standard methods known in the art. For example, an appropriate ion exchange resin may be employed to generate the desired salt. Alternatively, conversion of a trifluoroacetic acid salt to the parent free amine may be accomplished by standard methods known in the art (e.g., neutralization with an appropriate inorganic base such as $NaHCO_3$). Other desired amine salts may then be prepared in a conventional manner by reacting the free base with a suitable organic or inorganic acid. Representative pharmaceutically acceptable quaternary ammonium salts include the following: hydrochloride, sulfate, phosphate, carbonate, acetate, tartrate, citrate, malate, succinate, lactate, stearate, fumarate, hippurate, maleate, gluconate, ascorbate, adipate, gluceptate, glutamate, glucoronate, propionate, benzoate, mesylate, tosylate, oleate, lactobionate, laurylsulfate, besylate, caprylate, isetionate, gentisate, malonate, napsylate, edisylate, pamoate, xinafoate, napadisylate, hydrobromide, nitrate, oxalate, cinnamate, mandelate, undecylenate, and camsylate. Many of the compounds of Formula (I), (Ia), (II), and (IIa) carry an acidic carboxylic acid moiety, in which case suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope the use of prodrugs of Formula (I), (Ia), (II), and (IIa). In general, such prodrugs will be functional derivatives of the compounds, which are readily convertible in vivo into the required compound. Thus, in the methods of treatment of the present invention, the term "administering" shall encompass the treatment of the various conditions described with the compound specifically disclosed or with a compound that converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of the compounds of Formula (I), (Ia), (II), and (IIa) include active species produced upon introduction of the compounds into the biological milieu.

The term "administration" and variants thereof (e.g., "administering" a compound) mean providing a compound (optionally in the form of a salt or hydrate thereof) or a prodrug of the compound to the subject in need of treatment. When a compound of Formula (I), (Ia), (II), and (IIa) or pharmaceutically acceptable salt thereof or a hydrate or prodrug thereof is provided in combination with a second active agent (e.g., other antifungal and/or antibacterial agents useful for treating fungal and/or bacterial infections), "administration" and its variants are each understood to include concurrent and sequential provision of the compound (or the salt, hydrate, or prodrug thereof) and of the other active agent.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation, or experiment.

The term "effective amount" as used herein means an amount of active ingredient or pharmaceutical agent that elicits the biological or medicinal response in a tissue, system, animal, or human that is being sought by a researcher, veterinarian, medical doctor, or other clinician. In one embodiment, the "effective amount" can be a therapeutically effective amount that alleviates the symptoms of the disease or condition being treated. In another embodiment, the "effective amount" can be a prophylactically effective amount for prophylaxis of the symptoms of the disease or condition being prevented or for reducing the likelihood of occurrence. The term can also refer to an inhibition effective amount of the enfumafungin derivative sufficient to inhibit (1,3)-β-D-glucan synthase and thereby elicit the response being sought.

References to "treat," "treating," "treatment," and variants thereof, generally refer to a treatment that, after it is administered, results in resolution or improvement of one or more signs or symptoms associated with a fungal infection, or that results in eradication of the fungi responsible for an infection, or any combination of these outcomes.

For the purpose of treating and/or preventing PCP, the compound of Formula (I), (Ia), (II), or (IIa) (optionally in the form of a salt or a hydrate) can be administered in conventional ways available for use in conjunction with pharmaceuticals.

For the purpose of treating and/or preventing PCP, the compound of Formula (I), (Ia), (II), or (IIa) (optionally in the form of a salt or a hydrate) can be administered alone as an individual therapeutic agent or with one or more other antimicrobial agents (sequentially or concurrently) as a combination of therapeutic agents.

For the purpose of treating and/or preventing PCP, the compound of Formula (I), (Ia), (II), or (IIa) (optionally in the form of a salt or a hydrate) can be administered with a pharmaceutical carrier selected on the basis of the chosen route of administration and standard pharmaceutical practice.

For example, the compounds of Formula (I), (Ia), (II), and (IIa), and pharmaceutically salts and hydrate forms thereof, can be administered by one or more of the following routes: orally, parenterally (including subcutaneous injections, intravenous, intramuscular, intra-lesion injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose.

Further description of methods suitable for use in preparing pharmaceutical compositions and of ingredients suitable for use in said compositions is provided in Remington's Pharmaceutical Sciences, 20th edition, edited by A. R. Gennaro, Mack Publishing Co., 2000.

The compounds of Formula (I), (Ia), (II), and (IIa), and pharmaceutically acceptable salts and hydrate forms thereof, can be administered, e.g., orally or intravenously, in a dosage range of, for example, 0.001 to 1000 mg/kg of mammal (e.g., human) body weight per day in a single dose or in divided doses. An example of a dosage range is 0.01 to 500 mg/kg body weight per day orally or intravenously in a single dose or in divided doses. Another example of a dosage range is 0.1 to 50 mg/kg body weight per day orally or intravenously in single or divided doses. For oral administration, the compositions can be provided in the form of tablets or capsules containing, for example, 1.0 to 1000 milligrams of the active ingredient, particularly 1, 5, 10, 15, 20, 25, 50, 75, 100, 150, 200, 250, 300, 400, 500, 600, 750, and 1000 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For example, in embodiments, a pharmaceutically acceptable salt of the compound of Formula (IIa) is administered to a subject to provide a total daily dose of 150 to 1500 mg of the compound of Formula (IIa). In certain embodiments, a total daily dose of 150 mg, or a total daily dose of 250 mg, or a total daily dose of 500 mg, or a total daily dose of 750 mg, or a total daily dose of 1000 mg, or a total daily dose of 1500 mg of the compound of Formula (IIa) is administered: the total daily dose may be administered on a once-daily basis or it may be divided such as for BID (twice daily) dosing or TID (thrice daily) dosing or it may be administered less frequent such as three-times-a-week, twice-a-week or once-a-week particularly for treatment and/or the prevention of PCP. In embodiments, a pharmaceutically acceptable salt of the compound of Formula (IIa) is administered QD (once daily) or BID to provide 150 to 750 mg, or to provide 250 to 750 mg, or to provide 250 to 1000 mg, of the compound of Formula (IIa) per day.

In preferred embodiments, for treatment of *Pneumocystis* spp. pneumonia in a subject, the compound of Formula (IIa) or a pharmaceutically acceptable salt or hydrate thereof is administered orally and provides a total daily dose of from 250 mg to 1000 mg of the compound. In preferred embodiments, for treatment of *Pneumocystis* spp. pneumonia in a subject, the compound of Formula (IIa) or a pharmaceutically acceptable salt or hydrate thereof is administered for 2 to 6 weeks.

In preferred embodiments, for prevention of *Pneumocystis* spp. pneumonia in a subject, the compound of Formula (IIa) or a pharmaceutically acceptable salt or hydrate thereof is administered orally and provides a total daily dose of from 150 mg to 750 mg of the compound. In preferred embodiments, for prevention of *Pneumocystis* spp. pneumonia in a subject, the compound of Formula (IIa) or a pharmaceutically acceptable salt or hydrate thereof is administered for 4 weeks or more.

Antifungal activity of compounds against *Pneumocystis* spp. can be demonstrated by various assays known in the art, for example, by prophylaxis or treatment model of *Pneumocystis murina* pneumonia in mice. The activity of the compound is typically assessed by measuring survival and lung fungal burden as indicated by quantitative assessment of cyst (a.k.a. asci) and trophic (a.k.a. nuclei) forms of the *Pneumocystis* in lung. *Pneumocystis* spp. cannot be cultured in vitro for a long enough time to allow for in vitro antifungal evaluations, and murine models of *Pneumocystis* infection are considered the best alternative. *Pneumocystis* spp. has species specificity according to the mammal they infect. *Pneumocystis jirovecii*, the species responsible for infection in humans, does not efficiently infect mice. *Pneumocystis murina* is the species specific to mice. Immune and physiopathology considerations for murine models of PCP are considered applicable to human infection.

The present invention provides methods of treating *Pneumocystis* spp. pneumonia in a subject, comprising administering a triterpenoid antifungal agent to the subject. In embodiments, the triterpenoid antifungal agent is ibrexafungerp. In embodiments, the *Pneumocystis* species is *P. jirovecii*. In embodiments, the ibrexafungerp is administered orally. In embodiments, troph burden and cyst burden are both reduced.

The present invention further provides methods of preventing *Pneumocystis* spp. pneumonia in a subject, comprising administering a triterpenoid antifungal agent to the subject. In embodiments, the triterpenoid antifungal agent is ibrexafungerp. In embodiments, the *Pneumocystis* species is *P. jirovecii*. In embodiments, the ibrexafungerp is administered orally. In embodiments, troph burden and cyst burden are both reduced.

EXAMPLES

The following examples serve only to illustrate the invention and its practice. The examples are not to be construed as limitations on the scope or spirit of the invention.

Example 1

Evaluation of the effect of SCY-078 in a mouse model of prophylaxis for PCP.

The purpose of this study was to assess the efficacy of orally administered SCY-078 (ibrexafungerp) in preventing PCP, using the standard of care TMP-SMX as comparator.

Materials and Methods

Compound Preparation: SCY-078 (ibrexafungerp) was prepared in 0.5% methyl cellulose for oral administration. A correction factor of 1.37 for this lot was taken into account for salt and water content. Mice in the high dose group received 0.6 mg of SCY-078 BID, mid dose group received 0.3 mg of SCY-078 BID, and low dose group received 0.15 mg of SCY-078 BID, based on average mouse weights of 20 g.

Study design (groups): The study groups were as follows.

| Group | Drug regimen | Dose Schedule | # mice |
|---|---|---|---|
| 1 | Corticosteroid immunosuppressed (C/S) only/vehicle (Non-Treated Control) | — | 10 |
| 2 | C/S + SCY-078 High dose | 30 mg/kg/BID (6 wk) | 10 |
| 3 | C/S + SCY-078 Mid dose | 15 mg/kg/BID (6 wk) | 10 |
| 4 | C/S + SCY-078 Low dose | 7.5 mg/kg/BID (6 wk) | 10 |
| 5 | C/S + TMP/SMX | 50/250 mg/kg/3x/wk | 10 |
| Total # mice | | | 50 |

*P. murina* prophylaxis study method: C3H/HeN mice (Charles River) were infected by intranasal inoculation of *P. murina* organisms at $2\times10^6$/50 µl from a liquid nitrogen repository. Prior to inoculation, the *P. murina* were pre-incubated overnight in RPMI 1640 medium supplemented with calf serum and antibiotics to eliminate any bacterial contamination. The immune systems of the mice were suppressed by the addition of dexamethasone at 4 mg/liter to acidified drinking water (hydrochloric acid at 1 ml/liter). Acidification is used to prevent secondary microbial infections. The mice were divided into a negative (non-treated) control group (control steroid—C/S), positive control group (trimethoprim/sulfamethoxazole—TMP/SMX) and treatment groups. SCY-078 was administered orally (po) BID at the specified doses. The mice were started on the prophylaxis regimen at the same time they were inoculated. Immune suppression and treatment continued for the entire 6-week study. At the conclusion of that time, the mice were euthanized by $CO_2$ and lungs processed for analysis by homogenization. Slides were made from the lung homogenates at different dilutions and stained with Diff-Quik to quantify total nuclei (trophic forms) and with cresyl echt violet to quantify the asci (cyst forms).

Calculations: Efficacy was based on the reduction of organism burden between the treatment groups and the negative control group as determined by microscopic evaluation. The nuclei and asci counts for each lung were log transformed and statistical analysis was determined by the analysis of variance (ANOVA); individual groups were compared by the Student-Newman-Keuls t test for multiple comparisons using GraphPad Prism. Statistical significance was accepted at a P value≤0.05.

Results

FIG. 1 shows $\log_{10}$ mean nuclei and asci counts after 6 weeks of treatment. C/S refers to vehicle treated negative control. TMP/SMX refers to trimethoprim/sulfamethaxozole. Bracket denotes statistically significant difference between treatment groups and C/S group. #denotes no statistically significant difference between treatment group and TMP/SMX. Significance was accepted at a P value≤0.05.

As illustrated in FIG. 1, prophylaxis administration of SCY-078 resulted in a statistically significant reduction of both nuclei and asci counts when compared to untreated controls. There was a good dose-response correlation. The efficacy of the highest SCY-078 dose was comparable to the gold standard, TMP/SMX.

Percent Survival by treatment group and by week is illustrated in the table below, with * denoting statistically significant difference between treatment group and C/S group. Although this model is not typically associated with high mortality, SCY-078 dose regimens showed survival rate better than untreated controls and comparable to TMP/SMX, as shown in the table.

| Treatment | Percent Survival at | | | | | |
|---|---|---|---|---|---|---|
| group | Day 7 | Day 14 | Day 21 | Day 28 | Day 35 | Day 42 |
| Control/Steroid (C/S) | 100 | 90 | 90 | 90 | 80 | 60 |
| SCY-078 30 mg/kg BID | 100 | 100 | 100 | 100 | 100 | 100* |
| SCY-078 15 mg/kg BID | 100 | 90 | 90 | 80 | 80 | 80 |
| SCY-078 7.5 mg/kg BID | 100 | 90 | 90 | 90 | 90 | 90 |
| TMP/SMX | 100 | 90 | 90 | 90 | 90 | 90 |

Conclusions

SCY-078 at all 3 doses performed exceptionally well in this mouse prophylaxis model of *P. murina* pneumonia.

SCY-078 at all 3 dose levels significantly reduced both nuclei and asci burden versus the vehicle treated negative control group (C/S).

SCY-078 at 30 mg/kg performed equally as well at reducing the asci burden as the gold standard for treatment of *Pneumocystis* pneumonia, TMP/SMX.

SCY-078 at 30 mg/kg showed a significant improvement in survival versus the vehicle treated negative control group.

In this PCP prophylaxis model, SCY-078 showed potent antifungal activity against both cyst and trophic forms of *P. murina.*

SCY-078 represents a viable potential prophylaxis candidate to treat *Pneumocystis* pneumonia in humans.

Example 2

Evaluation of the effect of SCY-078 in a mouse model of treatment of PCP (early response).

The purpose of this study was to assess the efficacy of orally administered SCY-078 in treating PCP, focusing on early timepoints of response (Days 7, 14, and 21) using the standard of care TMP/SMX as comparator.

Methods

Compound Preparation: SCY-078 (ibrexafungerp) was prepared in 0.5% methyl cellulose for oral administration. A correction factor of 1.37 was taken into account for salt and water content. Mice in the high dose group received 0.3 mg of ibrexafungerp BID and mice in the low dose group received 0.1 mg of ibrexafungerp BID, based on average mouse weights of 20 g.

Study design (groups): The study groups were as follows.

| Group | Drug | Dose | Treatment Days | # of Animals |
|---|---|---|---|---|
| 1 | Negative Control | — | 7 | 10 |
| 2 | " | — | 14 | 10 |
| 3 | " | — | 21 | 10 |
| 4 | SCY-078 | 30 mg/kg/BID | 7 | 10 |
| 5 | " | " | 14 | 10 |
| 6 | " | " | 21 | 10 |

-continued

| Group | Drug | Dose | Treatment Days | # of Animals |
|---|---|---|---|---|
| 7 | SCY-078 | 15 mg/kg/BID | 7 | 10 |
| 8 | " | " | 14 | 10 |
| 9 | " | " | 21 | 10 |
| 10 | TMP/ SMX | 50/250 mg/kg/d | 7 | 10 |
| 11 | " | " | 14 | 10 |
| 12 | " | " | 21 | 10 |

*P. murina* treatment study methods: $C_3H/HeN$ mice ordered from Charles River were infected with *P. murina* pneumonia through exposure to mice with a fulminant *P. murina* infection (seed mice). These mice were immune suppressed by the addition of dexamethasone at 4 mg/liter to the drinking water. Sulfuric acid at 1 ml/liter was also added to the drinking water for disinfection. The seed mice were rotated within the cages for 2 weeks and then removed. After the mice developed a moderate infection level (approximately 5 weeks), they were divided into a negative control group (control steroid), positive control group (TMP/SMX) and treatment groups. Drugs to be tested were administered by oral gavage (PO) on a mg/kg/day basis for up to 3 weeks. At the end of the treatment, the mice were euthanized by $CO_2$ and lungs were processed for analysis. Slides were made from the lung homogenates at different dilutions and stained with Diff-Quik to quantify the nuclei (all life cycle stages) and with cresyl echt violet to quantify the asci.

Calculations: Efficacy was based on the reduction of organism burden between the treatment groups and the negative control group as determined by microscopic evaluation. The nuclei and asci counts for each lung were log transformed and statistical analysis was determined by the analysis of variance (ANOVA); individual groups were compared by the Student-Newman-Keuls t test for multiple comparisons using GraphPad Prism. Statistical significance was accepted at a P value$\leq$0.05.

Results

FIG. 2 shows $\log_{10}$ mean nuclei and asci counts after 7, 14 and 21 days of treatment. C/S refers to vehicle treated negative control. TMP/SMX refers to trimethoprim/sulfamethoxazole. Bracket denotes statistically significant difference between treatment groups and C/S group. #denotes statistically significant difference between treatment group and TMP/SMX. Significance was accepted at a P value$\leq$0.05.

As illustrated in FIG. 2, SCY-078 at both dose levels significantly reduced asci burdens versus the vehicle treated negative control group (C/S) at Day 14 and Day 21 evaluations, to a similar extent as compared with the gold standard for treatment of *Pneumocystis* pneumonia, TMP/SMX. SCY-078 at both dose levels performed statistically significantly better at reducing the asci burden at day 7 than the gold standard, TMP/SMX. SCY-078 at both dose levels significantly reduced nuclei burdens versus the vehicle treated negative control group (C/S) at Day 14 and Day 21 evaluations. The magnitude of the effect against nuclei burden was significant when compared to untreated controls though lower than observed with the TMP/SMX control. Survival was observed in 90% to 100% in all groups with no notable differences.

Conclusions

SCY-078 at both dose levels performed significantly better at reducing the asci burden at day 7 than the gold standard for treatment of *Pneumocystis* pneumonia, TMP/SMX.

SCY-078 at both dose levels significantly reduced both nuclei and asci burdens versus the vehicle treated negative control group (C/S) at day 14 and day 21.

In this PCP treatment model, SCY-078 showed potent antifungal activity against both cyst and trophic forms of *P. murina*.

SCY-078 is viable potential treatment option for *Pneumocystis* pneumonia in humans.

Since no dose response was seen between the two SCY-078 groups, a study using lower doses and longer follow-up duration was warranted.

Example 3

Evaluation of the effect of SCY-078 in a mouse model of treatment of PCP.

The purpose of this study was to assess the efficacy of orally administered SCY-078 in treating PCP, using the standard of care TMP-SMX as comparator.

Methods

Compound Preparation: SCY-078 (ibrexafungerp) was prepared in 0.5% methyl cellulose for oral administration. A correction factor of 1.37 was taken into account for salt and water content. Mice in the high dose group received 0.3 mg of ibrexafungerp BID and mice in the low dose group received 0.1 mg BID, based on average mouse weights of 20 g.

Study design (groups): The study groups were as follows.

| Group | Drug | Dose | Treatment Days | # of Animals |
|---|---|---|---|---|
| 1 | Negative Control | — | 21 | 10 |
| 2 | Ibrexafungerp | 15 mg/kg/BID | 28 | 10 |
| 3 | " | " | 35 | 10 |
| 4 | " | " | 42 | 10 |
| 5 | Ibrexafungerp | 10 mg/kg/BID | 28 | 10 |
| 6 | " | " | 35 | 10 |
| 7 | " | " | 42 | 10 |
| 8 | Ibrexafungerp | 5 mg/kg/BID | 28 | 10 |
| 9 | " | " | 35 | 10 |
| 10 | " | " | 42 | 10 |
| 11 | TMP/SMX | 50/250 mg/kg/d | 28 | 10 |
| 12 | " | " | 35 | 10 |
| 13 | " | " | 42 | 10 |

*P. murina* treatment study methods: Balb/c mice ordered from Charles River were infected with *P. murina* pneumonia through exposure to mice with a fulminant *P. murina* infection (seed mice). These mice were immune suppressed by the addition of dexamethasone at 4 mg/liter to the drinking water. Sulfuric acid at 1 ml/liter was also added to the drinking water for disinfection. The seed mice were rotated within the cages for 2 weeks and then removed. After the mice developed a moderate infection level (approximately 5 weeks), the mice were divided into a negative control group (control steroid), positive control group (TMP/SMX), and treatment groups. Drugs to be tested were administered by oral gavage (PO) on a mg/kg/BID basis for up to 6 weeks. At the end of the treatment, the mice were euthanized by $CO_2$ and lungs were processed for analysis. Slides were made from the lung homogenates at different dilutions and stained with Diff-Quik™ to quantify the nuclei (all life cycle stages) and with cresyl echt violet to quantify the asci.

Calculations: Efficacy was based on the reduction of organism burden between the treatment groups and the negative control group as determined by microscopic evaluation. The nuclei and asci counts for each lung were log transformed and statistical analysis was determined by the analysis of variance (ANOVA); individual groups were compared by the Student-Newman-Keuls t test for multiple comparisons using GraphPad Prism. Statistical significance was accepted at a P value≤0.05.

Results

FIG. 3 shows $\log_{10}$ mean nuclei and asci counts after 28, 35, and 42 days of treatment. C/S refers to vehicle treated negative control. TMP/SMX refers to trimethoprim/sulfamethoxazole. Bracket denotes statistically significant difference between treatment groups and C/S group. * denotes no statistically significant difference between treatment group and TMP/SMX. Significance was accepted at a P value≤0.05.

As illustrated in FIG. 3, SCY-078 at all dose levels significantly reduced both nuclei and asci burdens versus the vehicle treated negative control group (C/S) at all 3 timepoints.

Survival rates were between 90% and 100% for all of the SCY-078 and TMP/SMX treatment groups at 28, 35, and 42 days, with no statistical difference observed in survival.

Conclusions

SCY-078 at all dose levels significantly reduced both nuclei and asci burdens versus the vehicle treated negative control group (C/S) at all 3 timepoints.

SCY-078 at all dose levels worked equally well at reducing asci burden at day 42 as the positive control (TMP/SMX). At days 28 and 35, the 15 and 10 mg/kg groups worked equally as well at reducing asci burden as the positive control.

No asci were observed in the 15 and 10 mg/kg groups at days 28 and 35. However, some asci were observed in all 3 dose groups at day 42.

There was no statistical difference in survival between active treatment groups at any time point.

In this PCP treatment model, SCY-078 showed potent antifungal activity against both cyst and trophic forms of *P. murina.*

SCY-078 is viable potential treatment option for *Pneumocystis* pneumonia in humans.

While this invention has been particularly shown and described with references to preferred embodiments thereof, it will be understood in light of the present disclosure by those skilled in the art that various changes in form and details may be made therein without departing from the scope of the invention encompassed by the appended claims.

What is claimed is:

1. A method of treating *Pneumocystis* pneumonia in a subject in need thereof, the method comprising administering to the subject a compound of Formula (II):

(II)

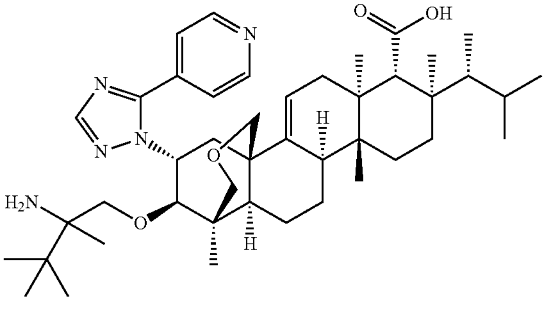

which is (1S,4aR,6aS,7R,8R, 10aR, 10bR, 12aR, 14R, 15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a, 10b, 11,12,12a-dodecahydro-1,6a,8,10a-tetramethyl-4H-1,4a-propano-2H-phenanthro [1,2-c]pyran-7-carboxylic acid, or a pharmaceutically acceptable salt or hydrate thereof.

2. The method according to claim 1, wherein the *Pneumocystis* pneumonia is caused by *Pneumocystis jirovecii.*

3. The method according to claim 2, wherein cyst burden and trophic burden of *Pneumocystis jirovecii* are reduced.

4. The method according to claim 1, wherein the compound or the pharmaceutically acceptable salt or hydrate thereof is administered orally.

5. The method according to claim 1, wherein the compound or the pharmaceutically acceptable salt or hydrate thereof is administered intravenously.

6. The method according to claim 1, wherein the subject is human.

7. A method of treating *Pneumocystis jirovecii* pneumonia in a human in need thereof, the method comprising administering to the human a compound of Formula (IIa):

(IIa)

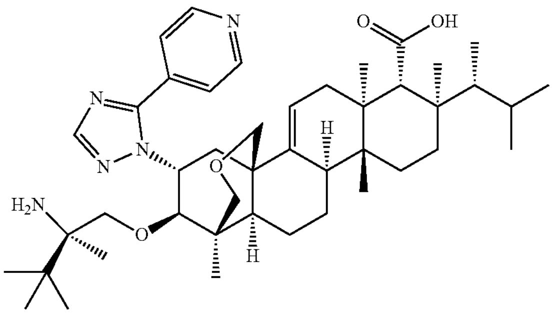

which is (1S,4aR,6aS,7R,8R, 10aR, 10bR, 12aR, 14R, 15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a, 10b, 11,12,12a-dodecahydro-1,6a,8,10a-tetramethyl-4H-1,4a-propano-2H-phenanthro [1,2-c]pyran-7-carboxylic acid, or a pharmaceutically acceptable salt or hydrate thereof.

8. The method according to claim 7, wherein cyst burden and trophic burden of *Pneumocystis jirovecii* are reduced.

9. The method according to claim 7, wherein the compound or the pharmaceutically acceptable salt or hydrate thereof is administered orally.

10. The method according to claim 7, wherein the compound or the pharmaceutically acceptable salt or hydrate thereof is administered intravenously.

11. The method according to claim 7, wherein the citrate salt of the compound of Formula (IIa) is administered.

12. The method according to claim 7, wherein the pharmaceutically acceptable salt of the compound of Formula (IIa) is administered orally in a tablet.

13. The method according to claim 7, wherein the compound or the pharmaceutically acceptable salt or hydrate thereof is administered orally and provides a total daily dose of from 250 mg to 1000 mg of the compound.

14. The method according to claim 13, wherein the compound or the pharmaceutically acceptable salt or hydrate thereof is administered for 2 to 6 weeks.

15. A method of treating *Pneumocystis jirovecii* pneumonia in a human in need thereof, the method comprising administering to the human a pharmaceutically acceptable salt of the compound of Formula (IIa):

(IIa)

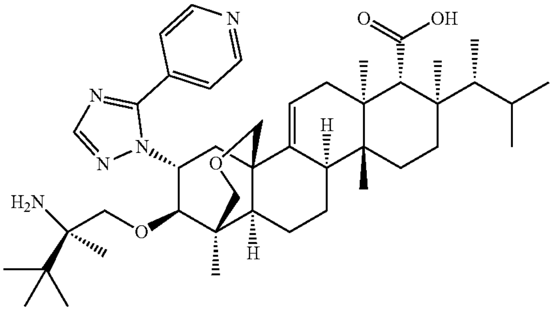

which is (1S,4aR,6aS,7R,8R,10aR, 10bR, 12aR,14R, 15R)-15-[[(2R)-2-amino-2,3,3-trimethylbutyl]oxy]-8-[(1R)-1,2-dimethylpropyl]-14-[5-(4-pyridinyl)-1H-1,2, 4-triazol-1-yl]-1,6,6a,7,8,9,10,10a, 10b, 11,12,12a-dodecahydro-1,6a,8,10a-tetramethyl-4H-1,4a-propano-2H-phenanthro [1,2-c]pyran-7-carboxylic acid.

16. The method according to claim 15, wherein the citrate salt of the compound of formula (IIa) is administered.

* * * * *